(12) United States Patent
Cap

(10) Patent No.: US 8,709,453 B2
(45) Date of Patent: Apr. 29, 2014

(54) COSMETIC PRODUCT INCLUDING VEGETABLE OIL BLEND

(75) Inventor: Daniel S. Cap, Streamwood, IL (US)

(73) Assignee: Daniel S. Cap, Maryville, TN (US)

( * ) Notice: Subject to any disclaimer, the term of this patent is extended or adjusted under 35 U.S.C. 154(b) by 2441 days.

(21) Appl. No.: 11/141,908

(22) Filed: Jun. 1, 2005

(65) Prior Publication Data

US 2005/0281851 A1    Dec. 22, 2005

Related U.S. Application Data

(60) Provisional application No. 60/581,440, filed on Jun. 21, 2004.

(51) Int. Cl.
| | |
|---|---|
| *A61K 8/36* | (2006.01) |
| *A61K 8/92* | (2006.01) |
| *A61Q 17/00* | (2006.01) |
| *A61Q 19/00* | (2006.01) |
| *A61Q 19/02* | (2006.01) |
| *A61Q 19/08* | (2006.01) |

(52) U.S. Cl.
CPC ............... *A61K 8/922* (2013.01); *A61K 8/361* (2013.01); *A61Q 17/00* (2013.01); *A61Q 19/007* (2013.01); *A61Q 19/02* (2013.01); *A61Q 19/08* (2013.01)
USPC ............................... 424/401; 424/59; 424/62

(58) Field of Classification Search
None
See application file for complete search history.

(56) References Cited

U.S. PATENT DOCUMENTS

| | | | |
|---|---|---|---|
| 3,900,503 A | 8/1975 | McNaught | |
| 4,108,879 A | 8/1978 | Minowa et al. | |
| 4,251,551 A * | 2/1981 | VanHulle et al. | 426/94 |
| 4,356,197 A * | 10/1982 | Devitt et al. | 426/89 |
| 4,393,043 A | 7/1983 | Koulbanis et al. | |
| 4,409,250 A * | 10/1983 | Van Hulle et al. | 426/242 |
| 4,649,057 A | 3/1987 | Thomson | |
| 4,902,527 A | 2/1990 | Galenkamp et al. | |
| 4,946,694 A * | 8/1990 | Gunnerson et al. | 426/273 |
| 5,024,831 A | 6/1991 | Kurisaki et al. | |
| 5,395,629 A | 3/1995 | Bertoli et al. | |
| 5,462,736 A * | 10/1995 | Rech et al. | 424/401 |
| 5,500,155 A * | 3/1996 | Weuthen et al. | 510/130 |
| 5,656,296 A | 8/1997 | Khan et al. | |
| 5,733,594 A * | 3/1998 | Hirose et al. | 426/611 |
| 6,190,079 B1 * | 2/2001 | Ruff | 401/201 |
| 6,229,056 B1 | 5/2001 | Ansmann et al. | |
| 6,284,257 B1 | 9/2001 | Khayat et al. | |
| 2001/0029047 A1 | 10/2001 | Liu et al. | |
| 2002/0053754 A1 * | 5/2002 | Katoh et al. | 264/171.13 |
| 2002/0157303 A1 | 10/2002 | Murphy et al. | |
| 2003/0012830 A1 * | 1/2003 | Small | 424/727 |
| 2003/0177691 A1 | 9/2003 | Stewart et al. | |
| 2004/0097392 A1 | 5/2004 | Connor et al. | |
| 2004/0191202 A1 * | 9/2004 | Murad | 424/70.13 |
| 2006/0275238 A1 * | 12/2006 | Blasko-Begoihn et al. | 424/70.13 |

FOREIGN PATENT DOCUMENTS

| | | |
|---|---|---|
| EP | 0 682 940 A1 | 11/1995 |
| JP | 60190705 | 9/1985 |
| WO | 97/28778 | 8/1997 |
| WO | 99/55657 | 11/1999 |
| WO | 99/63031 | 12/1999 |

OTHER PUBLICATIONS

Miller, "Miller's Homemade Soap Pages Design *Your Own* Recipe!", http://www.millersoap.com/soapdesign.html, last updated Nov. 18, 2003.*
http://www.crisco.com/Products/ProductDetail.aspx?groupID=17 &prodID=315 (2010).*
"Lotion" definitions from Webster's New World Coege Dictionary (Wiley Publishing, 2010) and The American Heritage Dictionary of the English Language, 4th ed. (Houghton Mifflin Harcourt Publishing, 2010), accessed Jan. 21, 2011.*
Soap qualities website (http:www.soapcalc.net/info/soapqualities. asp), accessed Jul. 5, 2011.*
Cates, Amy, "What is Solid Vegetable Shortening?", http://www.ehow.com/pring/facts_5676158_solid-vegetable-shortening.html, accessed Oct. 30, 2013.*

* cited by examiner

*Primary Examiner* — Daniel Sullivan
*Assistant Examiner* — Barbara Frazier
(74) *Attorney, Agent, or Firm* — Pauley Petersen & Erickson

(57) ABSTRACT

A cosmetic product includes a vegetable oil blend having an iodine value of 20-80 and including a partially hydrogenated vegetable oil and a fatty acid. The vegetable oil blend can be used alone or in combination with other ingredients. The vegetable oil blend moisturizes human skin, provides a protective barrier to dirt and weather, acts as an emollient, and may promote healing of cracked, dry or otherwise damaged skin.

29 Claims, No Drawings

COSMETIC PRODUCT INCLUDING VEGETABLE OIL BLEND

FIELD OF THE INVENTION

This invention is directed to a cosmetic product including a vegetable oil blend and having a variety of improved properties.

BACKGROUND OF THE INVENTION

Cosmetic compositions are compositions of products used to improve the appearance of human skin or hair. Examples of cosmetic products include without limitation skin lotions, creams, butters and balms; lip balms and creams; facial scrub compositions; hair conditioners and shampoos; after-shave lotions; bathwater oils and additives; and the like. One concern involving many cosmetic compositions is that, while they may improve the outward appearance of skin or hair, they have less healthy side effects including skin dryness and itching, scaling, hair dryness and splitting, pimple formation, etc.

In recent years, extensive research has been directed toward cosmetic compositions which not only improve the outward appearance of skin and hair, but also contribute to short-term and long-term health of skin and hair. To this end, various moisturizers, Vitamin E, Vitamin C, other antioxidants, aloe vera and the like have been added to cosmetic compositions.

While some of these additives have been more effective than others, the result has been a general improvement in the health benefits, and/or reduction in detrimental effects associated with using various cosmetic products. Work in this area is ongoing, and there is still a need for desire for additives which enhance the health benefits of cosmetic compositions.

SUMMARY OF THE INVENTION

The present invention is directed to a cosmetic toiletry product including a vegetable oil blend which includes a partially hydrogenated vegetable oil and additional fatty acid. The partially hydrogenated vegetable oil and additional fatty acid are present in amounts relative to each other such that the combination of partially hydrogenated vegetable oil and additional fatty acid (with no other ingredients) has an iodine value of about 20-80. The level of hydrogenation in the partially hydrogenated vegetable oil and the weight ratio of partially hydrogenated vegetable oil to additional fatty acid are selected so as to provide an iodine value (I.V.) within this range. Generally, the components are present in a weight ratio of about 50-95 parts by weight partially hydrogenated vegetable oil and about 5-50 parts by weight additional fatty acid.

The vegetable oil blend can be used alone or in a diluted cosmetic composition, in combination with other ingredients. When applied to human skin, the vegetable oil blend moisturizes the skin and provides a protective barrier to dust, dirt and weather. The vegetable oil blend acts as an emollient and may help promote healing of dry, cracked, or otherwise damaged skin.

When used in a diluted cosmetic composition, the vegetable oil blend may also serve as an emulsifier and emulsion stabilizer for other ingredients. Such cosmetic compositions may include about 1-99% by weight of the vegetable oil blend, suitably about 10-90% by weight. Diluted cosmetic compositions can be used to make cosmetic products, including without limitation skin lotions, creams, butters and balms; lip balms and creams; facial scrub products; hair conditioners and shampoos; bathwater oils and additives; medicinal creams; and the like.

With the foregoing in mind, it is a feature and advantage of the invention to provide new cosmetic compositions and products containing the vegetable oil blend as set forth herein.

DEFINITIONS

As used herein, "vegetable oil blend" refers to a blend that includes partially hydrogenated vegetable oil and additional fatty acid as described further below. The vegetable oil blend may include other ingredients as described below. The vegetable oil blend may also be combined with ingredients in addition to the vegetable oil blend.

As used herein, the term "cosmetic composition" refers to a composition used to make a cosmetic toiletry product. A "cosmetic toiletry product" is any product which improves the appearance of the health or skin, including without limitation skin lotions, creams, butters and balms; lip balms and creams; facial scrub compositions; hair conditioners and shampoos; after-shave lotions; bathwater oils and additives; medicinal creams (e.g., hydrocortisone cream); and the like. The cosmetic compositions of the invention may include the vegetable oil blend as the only component, or in addition to other ingredients.

As used herein, "diluted cosmetic composition" refers to a composition of a cosmetic toiletry product which includes the vegetable oil blend in addition to other ingredients.

As used herein, "iodine value" is the number of grams of iodine that an unsaturated compound or bend will absorb in a given time under arbitrary conditions. A low iodine value implies a high level of saturation, and vice-versa. The iodine value can be determined by the WIJS method of the American Oil Chemists' Society (A.O.C.S. Cd 1-25).

DETAILED DESCRIPTION OF THE PRESENTLY PREFERRED EMBODIMENTS

The invention is directed to a cosmetic composition and cosmetic toiletry products which include a vegetable oil blend. The vegetable oil blend includes a partially hydrogenated vegetable oil and additional free fatty acid in such weight proportions that the combination of partially hydrogenated vegetable oil and additional fatty acid (excluding other ingredients) has an iodine value of about 20-80, suitably about 30-70, particularly about 40-60, more particularly about 50. Generally, the iodine value of the combination is a function of the level of carbon-carbon unsaturation in the vegetable oil and in the additional fatty acid. Higher levels of hydrogenation (i.e., higher levels of saturation) in either or both components cause the combination to have lower iodine values.

Generally, the vegetable oil blend will include about 50-95 parts by weight partially hydrogenated vegetable oil and about 5-50 parts by weight additional fatty acid, based on the combined weight of the partially hydrogenated vegetable oil and fatty acid. The vegetable oil blend may include about 60-90 parts by weight partially hydrogenated vegetable oil and about 10-40 parts by weight additional fatty acid, or about 70-80 parts by weight partially hydrogenated vegetable oil and about 20-30 parts by weight additional fatty acid.

Suitable partially hydrogenated vegetable oils include any plant-based oil which has been partially hydrogenated. Examples include without limitation partially hydrogenated cottonseed oil, sunflower oil, canola oil, peanut oil, soybean oil, safflower oil, corn oil, palm oil, olive oil, coconut oil, palm kernel oil, almond oil, jojoba oil, avocado oil, sesame oil, castor oil, and combinations thereof. The term "partially hydrogenated vegetable oil" also includes mixtures of partially hydrogenated vegetable oil and fully hydrogenated vegetable oil. Such mixtures are, by definition, partially hydrogenated with an intermediate level of hydrogenation. Similarly, the term "partially hydrogenated vegetable oil" includes mixtures of partially hydrogenated vegetable oil and vegetable oil which has not been hydrogenated, and mixtures of fully hydrogenated and unhydrogenated vegetable oil. All such mixtures are partially hydrogenated. The partially hydrogenated vegetable oil may include one or more different vegetable oils having the same or different levels of hydrogenation.

The additional fatty acid may be any free fatty acid derived from vegetable oil, or otherwise synthesized, having from 12-22 carbon atoms. Examples of suitable fatty acids include without limitation lauric acid, myristic acid, palmitic acid, stearic acid, arachidic acid, palmitoleic acid, oleic acid, gadoleic acid, linoleic acid and combinations thereof. One example is a blend known as palm stearic acid, which includes about 50-56% by weight palmitic acid, about 41-47% by weight stearic acid, and a balance of other fatty acids.

The additional fatty acid component of the vegetable oil blend is a free fatty acid provided in addition to any free fatty acids inherently present in the partially hydrogenated vegetable oil. For instance, vegetable oils derived from natural sources typically include one or more triglycerides as a major component, lesser amounts of diglycerides and monoglycerides, and very minor amounts of free fatty acids. A triglyceride is an ester compound of glycerol linked to three fatty acid chains, and has the following general formula:

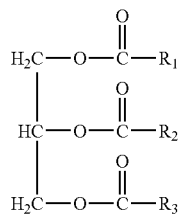

wherein $R_1$, $R_2$ and $R_3$ are fatty acid chains and may be the same or different.

A diglyceride is an ester compound of glycerol linked to two fatty acid chains. A monoglyceride is an ester composed of glycerol linked to one fatty acid chain. A free fatty acid is an unattached fatty acid in a vegetable oil, most commonly stearic acid and/or palmitic acid. The term "additional fatty acid" as used herein, and expressed in terms of amounts, refers to the quantity of free fatty acid combined with the vegetable oil to make the vegetable oil blend, over and beyond any naturally occurring amount (the latter being relatively insignificant).

The term "partially hydrogenated vegetable oil" refers to a vegetable oil which has been partially hydrogenated using known techniques for chemically adding hydrogen gas to a liquid vegetable oil in the presence of a catalyst. The process converts some of the unsaturated carbon-carbon double bonds in the vegetable oil molecules to single carbon-carbon bonds, thereby increasing the level of saturation. The degree of hydrogenation reflects the total number of double bonds which are converted. A vegetable oil that has been partially hydrogenated often retains a significant amount of unsaturation (reflected as carbon-carbon double bonds) in its molecular chains. The partial hydrogenation may cause partial saturation of the double bonds in any of the vegetable oil components, including triglycerides, diglycerides, monoglycerides and free fatty acids. The partial hydrogenation also relocates some of the double bonds to new locations, e.g., from a cis isomeric configuration to a trans isomeric configuration. Sufficient partial hydrogenation typically causes the vegetable oil to assume a solid or semi-solid state at ambient temperature (e.g., 25° C.).

As explained above, the iodine value of the vegetable oil blend reflects the number of grams of iodine which will react with 100 grams of vegetable oil blend. The vegetable oil blend used in the cosmetic composition (including partially hydrogenated vegetable oil and additional fatty acid) has an iodine value of about 20-80. By comparison, a completely unhydrogenated vegetable oil (e.g., soybean oil) may have an iodine value of about 125-140, and fully hydrogenated vegetable oils have iodine values near zero.

To make one suitable vegetable oil blend, having an iodine value of about 50, the following ingredients can be added in the stated preferred amounts:

|  | Range (%) | Preferred Amount (%) |
| --- | --- | --- |
| Soybean Oil | 0.01-7.00 | 1.00 |
| Hydrogenated Soybean Glycerides | 20.00-89.00 | 21.70 |
| Partially Hydrogenated Soybean Oil | 20.00-89.00 | 41.90 |
| Hydrogenated Palm Glycerides | 0.01-4.50 | 1.30 |
| Stearic Acid | 9.00-49.00 | 20.50 |
| Hydrogenated Soybean Oil | 3.50-15.00 | 10.40 |
| Palm Glycerides | 0.01-4.50 | 3.20 |

The vegetable oil blend can also be characterized in terms of its solid fat content ("SFC") as determined by differential scanning calorimetry using methods well known to persons skilled in the art. The vegetable oil blend may have a solid fat content at 10° C. ("SFC-10") of about 60-90% by weight, suitably about 67-85% by weight, particularly about 74-80% by weight. The vegetable oil blend may have a solid fat content at 21.1° C. (SFC-21.1) of about 40-70% by weight, suitably about 46-64% by weight, particularly about 52-58% by weight. The vegetable oil blend may have a solid fat content at 26.7° C. ("SFC-26.7") of about 25-55% by weight, suitably about 32-50% by weight, particularly about 39-44% by weight. The vegetable oil blend may have a solid fat content at 33.3° C. ("SFC-33.3") of about 15-40% by weight, suitably about 20-35% by weight, particularly about 25-29% by weight. The vegetable oil blend may have a solid fat content at 40° C. ("SFC-40") of about 3-25% by weight, suitably about 7-20% by weight, particularly about 12-16% by weight.

The vegetable oil blend can also be characterized in terms of its fatty acid composition. The fatty acid composition is the mixture of fatty acids that results or would result from complete hydrolysis of the triglycerides, diglycerides and monoglycerides in the vegetable oil blend. The fatty acid composition can be determined by methods known to persons skilled in the art, by gas chromatography analysis, or by conversion of the blend to a mixture of methyl esters followed by gas chromatography analysis.

In one embodiment, the vegetable oil blend may have the following fatty acid composition, expressed as CM:N, where M is the number of carbons in a fatty acid chain and N is the number of unsaturated carbon-carbon double bonds in the fatty acid chain.

| Fatty Acid | % By Weight | | |
|---|---|---|---|
| | Broad | Intermediate | Narrow |
| C14:0 | 0-10 | 0-5 | 0-1 |
| C16:0 | 10-40 | 15-35 | 20-30 |
| C16:1 | 0-10 | 0-5 | 0-1 |
| C17:0 | 0-10 | 0-5 | 0-1 |
| C17:1 | 0-10 | 0-5 | 0-1 |
| C18:0 | 5-35 | 10-30 | 15-25 |
| C18:1 | 30-70 | 35-65 | 40-55 |
| C18:2 | 0-20 | 1-10 | 2-8 |
| C18:3 | 0-10 | 0-5 | 0-1 |
| C20:0 | 0-10 | 0.1-5 | 0.2-1 |
| C20:1 | 0-10 | 0-5 | 0-1 |
| C22:0 | 0-10 | 0.1-5 | 0.2-1 |
| C24:0 | 0-10 | 0-5 | 0-1 |

In one embodiment, the vegetable oil blend is prepared separately and then either used alone as a cosmetic composition, or combined with additional ingredients to make a cosmetic composition. In another embodiment, the ingredients of the vegetable oil blend can be separately added to the cosmetic composition and combined with additional ingredients. In either instance, the vegetable oil blend ultimately forms all or part of the cosmetic composition. If the ingredients of the vegetable oil blend are separately added and combined with additional ingredients, then it may be desirable to make pre-blends of the vegetable oil blend in order to determine how much of each ingredient (partially hydrogenated vegetable oil and additional fatty acid) provides the vegetable oil blend with the desired iodine value and/or solid fat contents. Once the ingredients of the vegetable oil blend have been diluted with other ingredients of a cosmetic composition, it may be difficult to make this determination.

When the vegetable oil blend is prepared separately, it can be prepared by mixing the partially hydrogenated vegetable oil and fatty acid at a temperature of at least about 120° F., suitably about 125-200° F., particularly about 135-160° F. to form a substantially homogeneous blend. Any conventional mixer can be employed, such as a Hobart mixer or a steam-heated kettle equipped with a stirring device. The resulting vegetable oil blend can be cooled and granulated to form particles, powder, flakes, or other granules using conventional methods. Alternatively, the vegetable oil blend can be packaged and/or used as a liquid, or in any convenient form.

Depending on the type of cosmetic toiletry product, any amount of the vegetable oil blend may be employed. In one embodiment, the cosmetic toiletry product includes 95-100% by weight of the vegetable oil blend. In another embodiment, the cosmetic toiletry product includes 90% to less than 95% by weight of the vegetable oil blend. In another embodiment, the cosmetic toiletry product includes 80% to less than 90% by weight of the vegetable oil blend. In another embodiment, the cosmetic toiletry product includes 70% to less than 80% by weight of the vegetable oil blend. In another embodiment, the cosmetic toiletry product includes 60% to less than 70% by weight of the vegetable oil blend. In another embodiment, the cosmetic toiletry product includes 50% to less than 60% by weight of the vegetable oil blend. In another embodiment, the cosmetic toiletry product includes 40% to less than 50% by weight of the vegetable oil blend. In another embodiment, the cosmetic toiletry product includes 30% to less than 40% by weight of the vegetable oil blend. In another embodiment, the cosmetic toiletry product includes 20% to less than 30% by weight of the vegetable oil blend. In another embodiment, the cosmetic toiletry product includes 10% to less than 20% by weight of the vegetable oil blend. In another embodiment, the cosmetic toiletry product includes 5% to less than 10% by weight of the vegetable oil blend. In another embodiment, the cosmetic toiletry product includes 1% to less than 5% by weight of the vegetable oil blend.

The balance of each cosmetic toiletry product may be selected from a wide variety of ingredients conventionally used in formulating cosmetic compositions. These ingredients include without limitation emulsifiers, fragrances, rheology modifiers, ultraviolet radiation absorbers, aesthetic enhancing agents, solubilizing agents, anti-microbial agents, coloring agents and combinations thereof. The cosmetic composition may include water, and may be water-based. The amounts and types of additional ingredients will vary widely depending on the specific cosmetic composition. One skilled in the art would have the ability to determine the amounts and types of additional ingredients useful in a particular cosmetic composition.

Emulsifiers include without limitation emulsifying waxes, cetyl alcohol, cetearyl alcohol, polyolefin-glycol stearates, polysorbate, and the like. Fragrances include without limitation natural or synthetic perfumes, essential oils, floral fragrances, fruity fragrances, mint fragrances, fresh and clean fragrances, and the like. Rheology modifiers include without limitation magnesium aluminum silicates, cellulose gums, carbomer, and the like.

Ultraviolet radiation absorbers include without limitation octyl methoxycinnamate and benzophenone-3. Aesthetic enhancing agents include without limitation dimethicone and aluminum starch octenyl succinate. Solubilizing agents include without limitation $C_{12-15}$ alkyl benzoates and myristyl myristate. Coloring agents include without limitation titanium dioxide, iron oxide, pearling agents, and various dyes and pigments.

Other conventional ingredients include astringents (e.g., clove oil, menthol, camphor, eucalyptus oil, eugenol, menthyl lactate, witch hazel distillate), anti-acne agents (e.g., resorcinol, sulfur, salicylic acid, erythromycin, zinc), anti-caking agents, anti-foaming agents, antioxidants, binders, bulking agents, buffering agents, chelating agents, reducing agents, opacifying agents, propellants, skin bleaching agents, vitamins, and combinations thereof. The term "combinations thereof" refers to any combination including at least one of the listed ingredients. Water, when used, can constitute about 10-90% by weight of the cosmetic toiletry product, suitably about 50-85% by weight.

Additional ingredients (other than the vegetable oil blend) may collectively constitute 0-5% by weight, or greater than 5% to 10% by weight, or greater than 10% to 20% by weight, or greater than 20% to 30% by weight, or greater than 30% to 40% by weight, or greater than 40% to 50% by weight, or greater than 50% to 60% by weight, or greater than 60% to 70% by weight, or greater than 70% to 80% by weight, or greater than 80% to 90% by weight, or greater than 90% to 95% by weight, or greater than 95% to 99% by weight of the cosmetic toiletry product.

Cosmetic compositions can be prepared by mixing the vegetable oil blend, or ingredients of the vegetable oil blend, with additional cosmetic ingredients using a wide variety of techniques known to persons skilled in the art. In one embodiment, various cosmetic ingredients are combined together to form master-batches, each containing about 2-10 compatible ingredients. The cosmetic composition is then prepared by mixing together about 2-7 of the pre-formed masterbatches. The resulting cosmetic compositions often exist as emulsions, with each master-batch forming a separate phase. The resulting cosmetic composition can be formed into a cosmetic toiletry product having a liquid, gel or bar form.

EXAMPLES

The following cosmetic compositions can be made using a vegetable oil blend sold under the trade name SOYA SOFT SKIN™ by Natures Gifts, Inc. of Streamwood, Ill. This vegetable oil blend has an iodine value of about 50, and is composed of the following ingredients.

| Ingredient | % By Weight |
|---|---|
| Soybean Oil | 1.00 |
| Hydrogenated Soybean Glycerides | 21.70 |
| Partially Hydrogenated Soybean Oil | 41.90 |
| Hydrogenated Palm Glycerides | 1.30 |
| Stearic Acid | 20.50 |
| Hydrogenated Soybean Oil | 10.40 |
| Palm Glycerides | 3.20 |

Example 1

Lotion Bar

A lotion bar composed of 99.00% by weight SOYA SOFT SKIN™ and 1.00% by weight fragrance can be made by a) heating the SOYA SOFT SKIN™ to 70° C., then b) cooling it to 60° C., then c) adding the fragrance and mixing the ingredients thoroughly. The resulting cosmetic composition is poured into appropriate bar-shaped molds and allowed to cool and harden.

Example 2

Weather Protection Bar

A weather protection bar can be prepared having the following composition.

| | Ingredient | % By Weight |
|---|---|---|
| A | SOYA SOFT SKIN ™ | 91.00 |
| B | Beeswax | 4.00 |
| C | Almond Oil | 4.00 |
| D | Essential Oil Of Lavender | 1.00 |

To make the weather protection bar, ingredients A and B are mixed and heated to 70° C., then cooled to 60° C. Ingredients C and D are then added to ingredients A and B, and the combination is mixed thoroughly at 60° C. The resulting cosmetic composition is poured into appropriate bar shaped molds and permitted to cool and harden.

Example 3

Deodorant Stick

A deodorant stick can be prepared having the following composition.

| | Ingredient | % By Weight |
|---|---|---|
| A | SOYA SOFT SKIN ™ | 85.00 |
| B | Sodium Stearate | 7.00 |
| C | Calcium Sodium Phosphate and Mica | 4.00 |

-continued

| | Ingredient | % By Weight |
|---|---|---|
| D | Isosteareth-Z-Alcohol | 2.00 |
| E | Fragrance | 2.00 |

To make the deodorant stick, ingredient A is heated to 70° C., and mixed with ingredients B and C. The combination is allowed to cool to 60° C., and is mixed at 60° C. with ingredients D and E. Mixing of the five ingredients continues while the composition is cooled to 48° C. The resulting cosmetic composition is poured into appropriate containers and permitted to cool and harden.

Example 4

Protective Lip Balm

A protective lip balm can be prepared having the following composition.

| | Ingredient | % By Weight |
|---|---|---|
| A | SOYA SOFT SKIN ™ | 78.00 |
| B | Ceresin Wax | 8.00 |
| C | Beeswax | 8.00 |
| D | Octyl Methoxycinnamate | 3.00 |
| E | Distilled Water | 2.00 |
| F | Fragrance | 0.08 |
| D | Silica | 0.02 |

To make the protective lip balm, ingredients A, B and C are heated to 70° C. and mixed together. The combination is allowed to cool to 60° C. Ingredients D, E, F and G are added to the combination and mixed at 60° C. The composition is further mixed while cooling to 48° C. The resulting cosmetic composition is poured into appropriate containers and permitted to cool and harden.

Example 5

Zinc Oxide Stick

A zinc oxide stick can be prepared having the following composition.

| | Ingredient | % By Weight |
|---|---|---|
| A | SOYA SOFT SKIN ™ | 63.25 |
| B | Stearyl Alcohol | 15.00 |
| C | Zinc Oxide | 15.00 |
| D | Octyldodecyl Octyldodecanoate | 3.00 |
| E | Glycol Distearate | 1.50 |
| F | Glycerol Stearate and PEG-100 Alcohol | 1.50 |
| G | Perflouronony Dimethione | 0.75 |

To make the zinc oxide stick, ingredients A, B, D, E and F are heated to 70° C. and mixed together. The combination is permitted to cool to 60° C. Ingredients C and G are added to the combination and mixed at 60° C. The composition is further mixed while cooling to 50° C. The resulting cosmetic composition is poured into appropriate containers and permitted to cool and harden.

Example 6

Antiperspirant Stick

An antiperspirant stick can be prepared having the following composition.

| | Ingredient | % By Weight |
|---|---|---|
| A | SOYA SOFT SKIN ™ | 51.00 |
| B | Aluminum Zirconium Tetrachlorohydrex-gly | 20.00 |
| C | Stearyl Alcohol | 10.00 |
| D | PPG-3 Myristyl Ether | 7.00 |
| E | Hydrogenated Castor Oil | 6.00 |
| F | Dimethione and Dimethione Cross Polymer | 2.00 |
| G | Talc | 4.00 |

To make the antiperspirant stick, ingredients A, C, D, E and F are heated to 90° C. and mixed together. The combination is permitted to cool to 80° C. Ingredients B and G are added to the combination and mixed at 80° C. The composition is further mixed while cooling to 60° C. The resulting cosmetic composition is poured into appropriate containers and permitted to cool and harden.

Example 7

Body Butter

A body butter can be prepared having the following composition.

| | Ingredient | % By Weight |
|---|---|---|
| A | SOYA SOFT SKIN ™ | 48.00 |
| B | Distilled Water | 30.00 |
| C | Soy Distilled Monoglycerides | 10.00 |
| D | Glycerin | 5.00 |
| E | Beeswax | 4.00 |
| F | Avocado Oil | 2.00 |
| G | Fragrance | 1.00 |

To make the body butter, ingredients A, C, D, E and F are heated to 70° C. and mixed together. The combination is permitted to cool to 60° C. Ingredient B is added to the combination and mixed at 60° C. until uniform. Then, ingredient G is added and mixed while the composition is cooled to 55° C. The resulting cosmetic composition is poured into appropriate containers and permitted to cool.

Example 8

Basic Moisturizer

A basic skin moisturizer can be prepared having the following composition.

| | Ingredient | % By Weight |
|---|---|---|
| A | Distilled Water | 50.00 |
| B | SOYA SOFT SKIN ™ | 33.00 |
| C | Distilled Soy Monoglycerides | 10.00 |
| D | Glycerin | 3.00 |
| E | Mineral Oil | 3.00 |
| F | Lecithin | 1.00 |

To prepare the basic moisturizer, ingredients B, C, D, E and F are heated to 70° C. and mixed together. The combination is cooled to 60° C. Ingredient A is added to the combination and mixed at 60° C. until uniform. Mixing continues while the composition is cooled to 50° C. The resulting cosmetic composition is poured into appropriate containers and permitted to cool.

Example 9

SPF Lip Balm

A SPF protective lip balm can be prepared having the following composition.

| | Ingredient | % By Weight |
|---|---|---|
| A | SOYA SOFT SKIN ™ | 21.00 |
| B | Caprylic/Capric Triglyceride | 19.00 |
| C | Jojoba Oil | 12.20 |
| D | Candelilla Wax | 10.00 |
| E | Beeswax | 8.00 |
| F | Octyl Methoxycinnamate | 7.50 |
| G | Aloe Barbadensis Oil | 7.00 |
| H | Chamomile Oil | 6.00 |
| I | Carrot Extract | 5.00 |
| J | Benzophenone-3 | 3.00 |
| K | Cocoa Butter | 1.00 |
| L | Peppermint Oil | 0.20 |
| M | Propylparaben | 0.10 |

To prepare the protective lip balm, ingredients A, C, D, E, G, H and K are heated to 70° C. and mixed together. The combination is cooled to 60° C. Ingredients B, F, J and M are added to the combination at 60° C. and mixed until uniform. Ingredients I and L are then added, and the composition is further mixed while cooling to 50° C. The resulting cosmetic composition is poured into appropriate containers and permitted to cool and harden.

Example 10

Natural Skin Lotion

A natural skin lotion can be prepared having the following composition.

| | Ingredient | % By Weight |
|---|---|---|
| A | Distilled Water | 53.20 |
| B | SOYA SOFT SKIN ™ | 11.50 |
| C | Glyceryl Stearate, Celearyl Alcohol and Sodium Stearoyl Lactylate | 7.00 |
| D | Distilled Soy Monoglycerides | 10.00 |
| E | Sweet Almond Oil | 5.00 |
| F | Saccharomyces Cerevisiae | 4.00 |
| G | Jojoba Oil | 3.00 |
| H | Peppermint Leaf Oil | 3.00 |
| I | Glycerin | 2.00 |
| J | Hydrolyzed Oat Flour | 1.00 |
| K | Methylparaben | 0.20 |
| L | Propylparaben | 0.10 |
| M | Sodium Hydroxide | Trace |

To prepare the natural skin lotion, ingredient J is slowly dispersed into ingredient A while heating to 85° C. The mixture is held at 85° C. for a few minutes. Then, ingredients A, C, G, I, K and L are added and mixed at 85° C. to form a uniform water phase. Ingredients B, D, E and G are separately heated to 70° C. and mixed to form a uniform oil phase. The oil phase is added to the water phase with agitation, and the resulting emulsion is cooled to below 40° C. with agitation. Ingredients F and H are then added to the emulsion and mixed. The pH is adjusted by adding ingredient M. The resulting cosmetic composition is poured into appropriate containers.

Example 11

Soft Face Cream

A soft face cream can be prepared from the following composition.

|   | Ingredient | % By Weight |
|---|---|---|
| A | Distilled Water | 75.50 |
| B | SOYA SOFT SKIN ™ | 6.00 |
| C | Glycerin | 4.00 |
| D | Cetostearyl Alcohol | 4.00 |
| E | Isopropyl Palmitate | 3.90 |
| F | Octyl Dodecanol | 2.00 |
| G | Dimethione | 1.10 |
| H | Steareth-100, Steareth-2, Glyceryl Stearate Citrate, Sucrose, Mannan, and Xanthan Gum | 1.00 |
| I | Isostearyl Isostearate | 1.00 |
| J | Isohexadecane | 1.00 |
| K | Fragrance | 0.50 |

To make the soft face cream, ingredient A is slowly dispersed and mixed into ingredient H. Ingredient C is added. The mixture is heated to 80° C. Ingredients B, D, E, F, G, I and J are separately heated to 80° C. and then mixed with ingredients A, C and H until a homogeneous composition is formed. The composition is cooled to room temperature while stirring. Ingredient K is then added and mixed. The resulting cosmetic composition is stirred until smooth, and added to appropriate containers Example 12

Body Scrub

A body scrub can be prepared having the following composition.

|   | Ingredient | % By Weight |
|---|---|---|
| A | Distilled Water | 54.70 |
| B | Distilled Water with 2% Carbomer | 10.00 |
| C | Polyethylene 50 PC Microscrub Powder | 10.00 |
| D | Neoneatyl Glycol Dicaprylate/Dicaprate | 8.00 |
| E | Glycerin Stearate and PEG-100 Stearate | 6.00 |
| F | Isoeicosane | 5.00 |
| G | SOYA SOFT SKIN ™ | 3.00 |
| H | Glycerin | 2.00 |
| I | Stearyl Alcohol | 1.00 |
| J | Triethamolamine (99%) | 0.30 |

To make the body scrub, ingredients A, B and H are mixed and heated to 70° C. Ingredients D, E, F, G and I are separately mixed and heated to 75° C. The combination of ingredients A, B and H is then added to the combination of ingredients D, E, F, G and I. The resulting composition is thoroughly mixed and held at 75° C. for 15 minutes. Ingredient C is added to the composition and mixed until uniform. Then, ingredient J is added to the composition and mixed until uniform. The composition is then further mixed while cooling to 28° C. The resulting cosmetic composition is added to appropriate containers.

While the embodiments of the invention disclosed herein are presently preferred, various modifications and improvements can be made without departing from the spirit and scope of the invention. The scope of the invention is indicated by the appended claims, and all changes that fall within the meaning and range of equivalents are intended to be embraced therein.

I claim:

1. A cosmetic lotion product comprising at least 80% by weight of a vegetable oil blend, the vegetable oil blend selected from the group consisting of combinations of vegetable oil ingredients that include a partially hydrogenated vegetable oil and an additional fatty acid, the vegetable oil blend having an iodine value of 20-80, a solid fat content at 21.1° C. of 40-70% by weight and a fatty acid composition that includes 10-60% by weight C16:0, 5-35% by weight C18:0 and 30-70% by weight C18:1; and up to 20% by weight of one or more additional ingredients;

wherein the vegetable oil blend comprises at least about 20% by weight hydrogenated soybean glycerides, at least about 20% by weight partially hydrogenated soybean oil, about 9-49% by weight stearic acid, and about 3.5-15% by weight hydrogenated soybean oil; the cosmetic lotion product comprises a hardened, bar-shaped lotion bar; and wherein one or more of the additional ingredients is selected from the group consisting of fragrances, ultraviolet radiation absorbers, astringents, anti-acne agents, skin bleaching agents, and combinations thereof.

2. The cosmetic lotion product of claim 1, wherein the vegetable oil blend has an iodine value of about 30-70.

3. The cosmetic lotion product of claim 1, wherein the vegetable oil blend has an iodine value of about 40-60.

4. The cosmetic lotion product of claim 1, wherein the one or more additional ingredients further comprises at least one ingredient selected from the group consisting of emulsifiers, rheology modifiers, aesthetic enhancing agents, stabilizing agents, anti-microbial agents, coloring agents, anti-foaming agents, antioxidants, binders, bulking agents, buffering agents, chelating agents, reducing agents, opacifying agents, propellants, vitamins, water, and combinations thereof.

5. The cosmetic lotion product of claim 4, comprising up to 10% by weight of the one or more additional ingredients.

6. The cosmetic lotion product of claim 1, wherein the partially hydrogenated vegetable oil further comprises partially hydrogenated cottonseed oil.

7. The cosmetic lotion product of claim 1, wherein the partially hydrogenated vegetable oil further comprises partially hydrogenated sunflower oil.

8. The cosmetic lotion product of claim 1, wherein the partially hydrogenated vegetable oil further comprises partially hydrogenated peanut oil.

9. The cosmetic lotion product of claim 1, wherein the partially hydrogenated vegetable oil further comprises partially hydrogenated safflower oil.

10. The cosmetic lotion product of claim 1, wherein the partially hydrogenated vegetable oil further comprises partially hydrogenated canola oil.

11. The cosmetic lotion product of claim 1, wherein the partially hydrogenated vegetable oil further comprises partially hydrogenated corn oil.

12. The cosmetic lotion product of claim 1, wherein the partially hydrogenated vegetable oil further comprises partially hydrogenated palm oil.

13. The cosmetic lotion product of claim 1, wherein the partially hydrogenated vegetable oil further comprises partially hydrogenated olive oil.

14. The cosmetic lotion product of claim 1, wherein the partially hydrogenated vegetable oil further comprises partially hydrogenated coconut oil.

15. The cosmetic lotion product of claim 1, wherein the partially hydrogenated vegetable oil further comprises partially hydrogenated palm kernel oil.

16. The cosmetic lotion product of claim 1, wherein the partially hydrogenated vegetable oil further comprises partially hydrogenated almond oil.

17. The cosmetic lotion product of claim 1, wherein the partially hydrogenated vegetable oil further comprises partially hydrogenated jojoba oil.

18. The cosmetic lotion product of claim 1, wherein the partially hydrogenated vegetable oil further comprises partially hydrogenated avocado oil.

19. The cosmetic lotion product of claim 1, wherein the partially hydrogenated vegetable oil further comprises partially hydrogenated sesame oil.

20. The cosmetic lotion product of claim 1, wherein the partially hydrogenated vegetable oil further comprises partially hydrogenated castor oil.

21. The cosmetic lotion product of claim 1, wherein the additional fatty acid further comprises palmitic acid.

22. The cosmetic lotion product of claim 21, wherein the additional fatty acid further comprises oleic acid.

23. The cosmetic lotion product of claim 22, wherein the additional fatty acid further comprises linoleic acid.

24. The cosmetic lotion product of claim 23, wherein the additional fatty acid further comprises gadoleic acid.

25. The cosmetic lotion product of claim 24, wherein the additional fatty acid further comprises myristic acid.

26. The cosmetic lotion product of claim 25, wherein the additional fatty acid further comprises lauric acid.

27. The cosmetic lotion product of claim 1, wherein the vegetable oil blend has solid fat contents of about 60-90% by weight at 10° C., about 40-70% by weight at 21.1° C., about 25-55% by weight at 26.7° C., about 15-40% by weight at 33.3° C., and about 3-25% by weight at 40° C.

28. The cosmetic lotion product of claim 27, wherein the vegetable oil blend has solid fat contents of about 67-85% by weight at 10° C., about 46-64% by weight at 21.1° C., about 32-50% by weight at 26.7° C., about 20-35% by weight at 33.3° C., and about 7-20% by weight at 40° C.

29. The cosmetic lotion product of claim 27, wherein the vegetable oil blend has a solid fat content of about 74-80% by weight at 10° C., about 52-58% by weight at 21.1° C., about 39-44% by weight at 26.7° C., about 25-29% by weight at 33.3° C., and about 12-16% by weight at 40° C.

* * * * *